(12) United States Patent
Debreczeny et al.

(10) Patent No.: US 7,277,741 B2
(45) Date of Patent: Oct. 2, 2007

(54) PULSE OXIMETRY MOTION ARTIFACT REJECTION USING NEAR INFRARED ABSORPTION BY WATER

(75) Inventors: Martin Debreczeny, Danville, CA (US); Clark R. Baker, Jr., Castro Valley, CA (US)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 430 days.

(21) Appl. No.: 10/797,475

(22) Filed: Mar. 9, 2004

(65) Prior Publication Data

US 2005/0203357 A1    Sep. 15, 2005

(51) Int. Cl.
*A61B 5/00* (2006.01)
*A61B 5/02* (2006.01)

(52) U.S. Cl. .................................. 600/336; 600/502
(58) Field of Classification Search ............. 600/300, 600/336, 310, 322, 323, 500, 502
See application file for complete search history.

(56) References Cited

U.S. PATENT DOCUMENTS

| | | |
|---|---|---|
| 3,638,640 A | 2/1972 | Shaw |
| 3,998,550 A | 12/1976 | Konishi et al. |
| 4,066,068 A | 1/1978 | Nilsson et al. |
| 4,364,008 A | 12/1982 | Jacques |
| 4,711,244 A | 12/1987 | Kuzara |
| 4,714,341 A | 12/1987 | Hamaguri et al. |
| 4,723,554 A | 2/1988 | Oman et al. |
| 4,805,365 A | 2/1989 | Jobsis |
| 4,805,623 A * | 2/1989 | Jobsis .................. 600/328 |
| 4,850,365 A | 7/1989 | Rosenthal |
| 4,860,753 A | 8/1989 | Amerena |

(Continued)

FOREIGN PATENT DOCUMENTS

CA    2353007 A1    6/2000

(Continued)

OTHER PUBLICATIONS

Wheeler, Owen H., "Near Infrared Spectra or Organic Compounds," Department of Chemistry, College of Agriculture and Mechanic Arts, University of Puerto Rico (Mar. 1929).

(Continued)

*Primary Examiner*—Eric F. Winakur
(74) *Attorney, Agent, or Firm*—Fletcher Yoder

(57) ABSTRACT

A method and an apparatus for measuring a physiological parameter, functioning based on obtaining a first signal derived from electromagnetic energy transmitted through a tissue portion at a first wavelength, the first signal including a signal portion corresponding with motion-related events and a signal portion corresponding with arterial pulsation events, where at the first wavelength water is a dominant absorber of electromagnetic energy in the tissue portion; obtaining a second signal derived from electromagnetic energy transmitted through a tissue portion at a second wavelength, the second signal including a signal portion corresponding with motion-related events and a signal portion corresponding with arterial pulsation events, where at the second wavelength hemoglobin is a dominant absorber of electromagnetic energy in the tissue portion; and combining the first signal and the second signal to generate a combined plethysmograph signal, such that the combined signal has a signal portion corresponding with motion-related events that is smaller than that present in the first signal or the second signal.

25 Claims, 7 Drawing Sheets

U.S. PATENT DOCUMENTS

| | | |
|---|---|---|
| 4,883,055 A | 11/1989 | Merrick |
| 4,907,594 A | 3/1990 | Muz |
| 4,911,167 A | 3/1990 | Corenman et al. |
| 4,936,679 A | 6/1990 | Mersch |
| 5,057,695 A | 10/1991 | Hirao et al. |
| 5,086,781 A | 2/1992 | Bookspan |
| 5,111,817 A | 5/1992 | Clark et al. |
| 5,146,091 A | 9/1992 | Knudson |
| 5,224,478 A | 7/1993 | Sakai et al. |
| 5,277,181 A | 1/1994 | Mendelson et al. |
| 5,279,295 A | 1/1994 | Martens et al. |
| 5,282,467 A | 2/1994 | Piantadosi et al. |
| 5,297,548 A * | 3/1994 | Pologe ................. 600/310 |
| 5,337,745 A | 8/1994 | Benaron |
| 5,337,937 A | 8/1994 | Blank et al. |
| 5,348,004 A | 9/1994 | Hollub |
| 5,355,880 A | 10/1994 | Thomas et al. |
| 5,377,674 A | 1/1995 | Kuestner |
| 5,385,143 A | 1/1995 | Aoyagi |
| 5,482,036 A | 1/1996 | Diab et al. |
| 5,499,627 A | 3/1996 | Steuer et al. |
| 5,615,689 A | 4/1997 | Kotler |
| 5,645,059 A | 7/1997 | Fein et al. |
| 5,645,060 A | 7/1997 | Yorkey |
| 5,687,721 A | 11/1997 | Kuhls |
| 5,692,503 A | 12/1997 | Kuenstner |
| 5,701,902 A | 12/1997 | Vari et al. |
| 5,720,284 A | 2/1998 | Aoyagi et al. |
| 5,735,284 A | 4/1998 | Tsoglin et al. |
| 5,747,789 A | 5/1998 | Godik |
| 5,755,672 A | 5/1998 | Arai et al. |
| 5,788,643 A | 8/1998 | Feldman |
| 5,803,908 A | 9/1998 | Steuer et al. |
| 5,827,181 A | 10/1998 | Dias et al. |
| 5,833,602 A | 11/1998 | Osemwota |
| 5,842,981 A | 12/1998 | Larsen et al. |
| 5,853,364 A | 12/1998 | Baker, Jr. et al. |
| 5,860,919 A | 1/1999 | Kiani-Azarbayjany et al. |
| 5,906,582 A | 5/1999 | Kondo et al. |
| 6,064,898 A | 5/2000 | Aldrich |
| 6,125,297 A | 9/2000 | Siconolfi |
| 6,149,591 A | 11/2000 | Henderson et al. |
| 6,157,850 A * | 12/2000 | Diab et al. ................. 600/323 |
| 6,178,342 B1 | 1/2001 | Thompson et al. |
| 6,222,189 B1 | 4/2001 | Misner et al. |
| 6,246,894 B1 | 6/2001 | Steuer et al. |
| 6,266,546 B1 | 7/2001 | Steuer et al. |
| 6,280,396 B1 | 8/2001 | Clark et al. |
| 6,336,044 B1 | 1/2002 | Ghiassi et al. |
| 6,370,426 B1 | 4/2002 | Campbell et al. |
| 6,400,971 B1 | 6/2002 | Finarov et al. |
| 6,402,690 B1 | 6/2002 | Rhee et al. |
| 6,442,408 B1 | 8/2002 | Wenzel et al. |
| 6,466,807 B1 | 10/2002 | Dobson et al. |
| 6,488,677 B1 | 12/2002 | Bowman et al. |
| 6,501,975 B2 * | 12/2002 | Diab et al. ................. 600/336 |
| 6,512,936 B1 | 1/2003 | Monfre et al. |
| 6,591,122 B2 | 7/2003 | Schmitt |
| 6,592,574 B1 | 7/2003 | Shimmick et al. |
| 6,600,946 B1 | 7/2003 | Rice |
| 6,606,509 B2 | 8/2003 | Schmitt |
| 6,615,064 B1 | 9/2003 | Aldrich |
| 6,635,491 B1 | 10/2003 | Khalil et al. |
| 6,636,759 B2 | 10/2003 | Robinson |
| 6,643,543 B2 | 11/2003 | Takehara et al. |
| 6,654,620 B2 | 11/2003 | Wu et al. |
| 6,668,181 B2 | 12/2003 | Wenzel et al. |
| 6,675,029 B2 | 1/2004 | Monfre et al. |
| 6,687,519 B2 | 2/2004 | Steuer et al. |
| 6,777,240 B2 | 8/2004 | Hazen et al. |
| 6,849,046 B1 | 2/2005 | Eyal-Bickels |
| 6,950,699 B1 | 9/2005 | Manwaring et al. |
| 2001/0005773 A1 * | 6/2001 | Larsen et al. ................. 600/323 |
| 2001/0020122 A1 | 9/2001 | Steuer et al. |
| 2003/0060693 A1 | 3/2003 | Monfre et al. |
| 2004/0230106 A1 | 11/2004 | Schmitt et al. |

FOREIGN PATENT DOCUMENTS

| | | |
|---|---|---|
| DE | 19855521 A1 | 6/2000 |
| DE | 10213692 A1 | 10/2003 |
| EP | 1135184 A1 | 6/2000 |
| EP | 1184663 A2 | 3/2002 |
| FR | 2710517 | 4/1995 |
| JP | 4-40940 | 2/1992 |
| JP | 05-212016 | 8/1993 |
| JP | 5-329163 | 12/1993 |
| JP | 11-244266 | 9/1999 |
| WO | WO94/03102 | 2/1994 |
| WO | WO97/49330 | * 12/1997 |
| WO | WO98/34097 | 8/1998 |
| WO | WO 00/32262 A1 | 6/2000 |
| WO | WO 00/71025 A1 | 11/2000 |
| WO | WO93/13706 A2 | 1/2001 |
| WO | WO 01/16577 A1 | 3/2001 |

OTHER PUBLICATIONS

Pace, Nello, et al., "Stduies on Body Composition: III. The body water and chemically combined nitrogen content in relation to fat content," Naval Medical Research Institute, Bethesda, Maryland (Jan. 11, 1945).

Mitchell, H. M., et al., The Chemical Composition of the Adult Human Body and its bearing on the Biochemistry of Growth), Division of Animal Nutrition, Departments of Physiology and Animal Husbandry, University of Illinois, pp. 625-637 (Feb. 1945).

Schloerb, Paul R., et al., "The Measurement of Total Body Water in the Human Subject by Deuterium Oxide Dilution," *Surgical Research Laboratories of the Peter Bent Brigham Hospital, and the Department of Surgery and the Biophysical Laboratory of the Harvard Medical School*, pp. 1296-1310 (Mar. 20, 1950).

Forbes, R.M., et al., "The Composition of the Adult Human Body as Determined by Chemical Analysis," Division of Animal Nutrition, and the Department of Anatomy, University of Illinois, Jan. 19, 1953.

Buijs, K., et al., "Near-Infrared Studies of the Structure of Water. I. Pure Water," *The Journal of Chemical Physics*, vol. 39, No. 8, pp. 2035-2041 (Oct. 15, 1963).

Choppin, G.R., et al., "Near-Infrared Studies of the Structure of Water. II. Ionic Soluation," *The Journal of Chemical Physics*, vol. 39, No. 8, pp. 2042-2050 (Oct. 15, 1963).

Goldstein, R., et al., "The Near-Infrared Absorption of Liquid Water at Temperatures Between 27 and 209° C.," *J. Quant. Spectrosc. Radiat. Transfer.*, vol. 4, pp. 441-451 (1964).

Ben-Gera, I., et al., "Influence of Fat Concentration on the Absorption Spectrum of Milk in the Near-Infrared Region," *Israel J. Agric. Res.*, vol. 18, No. 3, pp. 117-124 (Jul. 1968).

Houseman, R.A., et al., "The measurement of total body water in living pigs by deuterium oxide dilution and its relation to body composition," *Br. J. Nutr.*, vol. 30, pp. 149-156 (1973).

Krikorian, S. Edward, et al., "The identification and origin of N-H overtone and combination bands in the near-infrared spectra of simple primary and secondary amides," *Spectrochimica Acta*, vol. 29A, pp. 1233-1246 (1973).

Lesser, G.T., et al., "Body water compartments with human aging using fat-free mass as the reference standard," *Am J. Physiol Regul Integr Comp Physiol.*, vol. 236, pp. 215-220 (1979).

Sheng, Hwai-Ping, et al., "A review of body composition studies with emphasis on total body water and fat," *The American Journal of Clinical Nutrition*, vol. 32., pp. 630-647 (Mar. 1979).

Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-149 (1980).

Fomon, Samuel J., et al., "Body composition of reference children from birth to age 10 years," The American Journal of clinical Nutrition, vol. 35, pp. 1169-1175, (May 1982).

Lanza, Elaine, "Determination of Moisture, Protein, Fat, and Calories in Raw Pork and Beef by near Infrared Spectroscopy," Journal of Food Science, vol. 48, pp. 471-474 (1983).

Martens, Harald, et al., "Understanding food research data," Food Research and Data Analysis, Applied Science Publishers, pp. 5-38 (1983).

Shields, R. G., Jr., et al., "Efficacy of Deuterium Oxide to Estimate Body Composition of Growing Swine"; Journal of Animal Science, vol. 57, No. 1, pp. 66-73, (1983).

Wolfgang, Arneth, "Multivariate Infrared and near-infrared Spectroscopy: rapid analysis of protein, fat and water in meat," Food Res and Data Analysis, Proc from IUoST Symp, Oslo, Norway, pp. 239-251 (1983).

Cohn, S.H., et al., "Assessment of cellular mass and lean body mass by noninvasive nuclear technqiues," J. Lab Clin Med., vol. 105, pp. 305-311 (1985).

Hannon, John P., et al., "Splenic red cell sequestration and blood volume measurements in conscious pigs," Am J. Physiol., vol. 248, pp. R293-R301 (1985).

Potts, R.O., et al., "A Noninvasive, In Vivo Technique to Quantitatively measure Water Concentration of the Stratum Corneum Using Attenuated Total-Reflectance Infrared Spectroscopy," Arch. Dermatol Res., vol. 277, pp. 489-495 (1985).

Cox, Patrick, et al., "Variations in Lipids in Different Layers of Porcine Epidermis," J. Invest Dermatol., vol. 87, pp. 741-744 (1986).

Valdes, E. V., et al., "Determination of Crude Protein and Fat in Carcass and Breast Muscle Samples of Poultry by Near Infrared Reflectance Spectroscopy," Poultry Science, vol. 65, pp. 485-490 (1986).

Hedberg, Christopher L., et al., "The Time Course of Lipid Biosynthesis in Pig Epidermis," J. Invest Dermatol., vol. 91, pp. 169-174 (1988).

Hedberg, Christopher L., et al., "The nonpolar Lipids of Pig Epidermis," J. Invest Dermatol., vol. 90, pp. 225-229 (1988).

Trapp, Scott A., et al., "An improved spectrophotometric bromide assay for the estimation of extracellular water volume," Clinica Chimica Acta., vol. 181, pp. 207-212, (1989).

Bommannan, D., et al., "Examination of Stratum Corneum Barrier Function In Vivo by Infrared Spectroscopy," J. Invest Dermatol, vol. 95, pp. 403-408 (1990).

Hannon, John P., et al., "Normal pHysiological Values for Conscious Pigs Used in Biomedical Research," Laboratory Animal Science, vol. 40, No. 3, May 1990.

Mak, Vivien H.W., et al., "Oleic Acid Concentration and Effect in Human Stratum Corneum: Non-Invasive determination By Attenuated Total Reflectance Infrared Spectroscopy In Vivo," Journal of Controlled Release, vol. 12, pp. 67-75 (1990).

Edwardson, P. et al., "The Use of FT-IR for the Determination of Stratum Corneum Hydration in Vitro and in Vivo," J. of Pharmaceutical & Biomed. Analysis, vol. 9, Nos. 10-12, pp. 1089-1094, 1991.

Drummer, C., et al., "Effects of an acute saline on fluid and electrolyte metabolism in humans," Am J. Physiol., vol. 262, pp. F744-F754 (1992).

Horber, F.F., et al., "Impact of hydration status on body composition as measured by dual energy X-ray absorptiometry in normal volunteers and patients on haemodialysis," The British Journal of Radiology, vol. 65, pp. 895-900 (1992).

Schmitt et al., Proc. SPIE, "Measurement of blood hematocrit by dual-wavelength near-IP photoplethysmography," 1641:150-161 (1992).

Diaz-Carrillo, E., et al., "Near infrared calibrations for goat's milk components; protein, total casein, $\alpha_s$, $\beta$- and $k$-caseins, fat and lactose," J. near Infrared Spectrosc., vol. 1, pp. 141-146 (1993).

Martin, K., "Direct Measurement of Moisture in Skin by NIR spectroscopy," J. Soc. Cosmet. Chem., 44:249-261 (1993).

Richard, Stèphanie, et al., "Characterization of the Skin In Vivo by High Resolution Magnetic Resonance Imaging: Water Behavior and Age-Related Effects," The Journal of Investigative Dermatology, vol. 100, No. 5, pp. 705-709 (May 1993).

Thompson et al., "Can bioelectrical impedance be used to measure total body water in dialysis patients?", Physiol. Meas., 14:455-461 (1993).

Bewig, Karen M., et al., "Discriminant Analysis of Vegetable Oils by Near-Infrared Reflectance Spectroscopy," JAOCS, vol. 71, No. 2, pp. 195-200 (Feb. 1994).

Kamishikiryo-Yamashita, Hiromi, et al, "Protein Content in Milk by Near-Infrared Spectroscopy," Journal of Food Science, vol. 59, No. 2, pp. 313-315 (1994).

Matcher, S. J., et al., "Absolute quantification of deoxyhaemoglobin concentration in tissue near infrared spectroscopy," Phys. Med. Biol., vol. 39, pp. 1295-1312 (1994).

Simanonok, Karl E., et al., "A Comprehensive Guyton Model Analysis of Physiologic Responses to Preadapting the Blood Volume as a Countermeasure to Fluid Shifts," J. Clin Pharmacol, vol. 34, pp. 440-453 (1994).

Steven, Alasdair C., et al., "Protein composition of cornified cell envelopes of epidermal keratinocytes," Journal of Cell Science, vol. 107, pp. 693-700 (1994).

Takeo, T. et al., "Skin Hydration State Estimation Using a Fiber-Optic Refractometer," Applied Optics, vol. 33, No. 19, Jul. 1994, p. 4267-72.

Warren, Joan L., et al., "The burden and Outcomes Associates with Dehydration among US Elderly, 1991," American Journal of Public Health, vol. 84, No. 8, pp. 1265-1269 (Aug. 1994).

Åneman, Anders, et al., "Splanchnic and Renal Sympathetic Activity in Relation to Hemodynamics During Isoflurane Administration in Pigs," Anesth Analg., vol. 80, pp. 135-142, (1995).

Kisch, Hille, et al., "Accuracy and reproducibility of the measurement of actively circulating blood volume with an integrated fiberoptic monitoring system," Critical Care Medicine, vol. 23, No. 5, pp. 885-893 (1995).

Isaksson, Tomas, et al., "Non-Destructive Determination of Fat, Moisture and Protein in Salmon Fillets by Use of Near-Infrared Diffuse Spectroscopy," J. Sci Food Agric., vol. 69, pp. 95-100 (1995).

Quiniou, N., et al., "Prediction of Tissular Body Composition from Protein and Lipid Deposition in Growing Pigs," J. Anim. Sci., vol. 73, pp. 1567-1575, (1995).

Avis, N. J., et al.; "In vitro multifrequency electrical impedance measurements and modeling of the cervix in late pregnancy"Physiological Measurement, vol. 17, pp. A97-103, 1996.

Gniadecka, M., et al., "Assessment of dermal water by high-frequency ultrasound: comparative studies with nuclear magnetic resonance," British Journal of Dermatology, vol. 135, pp. 218-224, (1996)

Finn, Patrick J., et al., "Progressive cellularl dehydration and proteolysis in critcally ill patients," The Lancet, vol. 347, pp. 654-646 (Mar. 9, 1996).

Johnson et al., "Monitoring of Extracellular and Total Body Water during Hemodialysis Using Multifrequency Bio-Electrical Impedance Analysis," Kidney and Blood Pressure Research, 19:94-99 (1996).

Kotler, D.P., et al.; "Prediction of body cell mass, fat-free mass, and total body water with bioelectrical impedance analysis: effects of race, sex, and disease;" Am. J. Clin. Nutr. 64(suppl):489S-97S(1996).

Kumar, Gitesh, et al., "Non-Invasive Optical Assessment of Tissue Hydration," International conferene on Biomedical Engineering, Jun. 3-5, 1996, Hong Kong, pp. C2-5.

Schmitt et al., Proc. SPIE, "Optimum wavelengths for measurement of blood hemoglobin content and tissue hydration by NIR spectrophotometry," 2678:442-453 (1996).

De Fijter, W.M., et al., "Assessment of total body water ad lean body mass from anthropometry, Watson formula, creatinine kinetics, and body electrical impedance compared with antipyrine kinetics and peritoneal dialysis patients," Nephrol Dial Transplant, vol. 12, pp. 151-156 (1997).

Johansen, Lars Bo, et al., "Hemodilution, central blood volume, and renal responses after an isotonic saline infusion in humans," Am J. Physiol., vol. 272, pp. R549-R556 (1997).

Visser, Marjolein, et al., "Density of fat-free body mass: relationship wth race, age, and level of body fatness," *Am J. Physiol.*, vol. 272, pp. E781-E787, (1997).

Alanen, Esko, et al., "Measurement of dielectric properties of subcutaneous fat with open-ended coaxial sensors," *Phys. Med. Biol.*, vol. 43, pp. 475-485 (1998).

Alanen, Esko, et al., "Variational Formulation of Open-Ended Coaxial line in Contact with Layered Biological Medium," *IEEE Transactions on Biomedical Engineering*, vol. 45, No. 10, pp. 1241-1248 (Oct. 1998).

Bonadonna, Riccardo C., et al., "Tole of Tissue Specific Blood Flow and Tissue Recruitment in Insulin-Mediated Glucose Uptake of Human Skeletal Muscl," *Circulation*, vol. 98, pp. 234-241, (1998).

Bracco, David, et al., "Bedside determination of fluid accumulation after cardiac surgery using segmental bioelectrical impedance," *Cri Care Med*, vol. 26, No. 6, pp. 1065-1070 (1998).

Gniadecka, Monika, et al., "Water and Protein Structure in Photoaged and Chronically Aged Skin," *J. Invest Dermatol*, vol. 111, pp. 1129-1133 (1998).

Gniadecka, Monika, et al., "Structure of Water, Proteins, and Lipids in Intact Human Skin, Hair, and Nail," *J. Invest Dermatol*, vol. 110, pp. 393-398 (1998).

Gow, Kenneth W., et al., "Effect of crystalloid administration on oxygen extraction in endotoxemic pigs," *J. Appl. Physiol.*, vol. 85, No. 5, pp. 1667-1675 (1998).

Husby, P., et al., "Midazolam-fentanyl-isoflurane anaesthesia is suitable for haemodynamic and fluid balance studies in pigs," *Laboratory Animals*, vol. 32, pp. 316-323 (1998).

Mitchell, A. D., et al., "Composition Analysis of Pork Carcasses by Dual-Energy X-Ray Absorptiometry," *J. Anim. Sci.*, vol. 76, pp. 2104-2114 (1998).

Mahan, D. C., et al., "Essential and Nonessential Amino Acid Composition of Pigs from Birth to 145 Kilograms of Body Weight, and Comparison to Other Studies," *J. Anim. Sci.*, vol. 76, pp. 513-521, (1998).

Martin, Kathleen, "In Vivo Measurements of Water in Skin by Near-Infrared Reflectance," *Applied Spectroscopy*, vol. 52, No. 7, 1998, pp. 1001-1007.

Schou, Henning, et al., "Uncompensated Blood Los is not Tolerated During Acute Normovolemic Hemodilution in Anesthetized Pigs," *Anesth Analg.*, vol. 87, pp. 786-794 (1998).

Stranc, M.F., et al., "Assessment of tissue viability using near-infrared spectroscopy," *British Journal of Plastic Surgery*, vol. 51, pp. 210-217, (1998).

Thomas, B. J., et al., "Bioimpedance Spectrometry in the Determination of Body Water Compartments: Accuracy and Clinical Significance," *Appl. Radiat. Isot.*, vol. 49, No. 5/6. pp. 447-455, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Vrhovski, Bernadette, et al., "Biochemistry of tropoelastin," *Eur. J. Biochem.*, vol. 258, pp. 1-18 (1998).

Alanen, Esko, et al., "Penetration of electromagnetic fields of an open-ended coaxial probe between 1 MHz and 1 GHz in dielectric skin measurements," *Phys. Med. Bio.*, vol. 44, pp. N169-N176 (1999).

Dickens, Brian, et al., "Estimation of Concentration and Bonding Environment of Water Dissolved in Common Solvents Using Near Infrared Absorptivity," *J. Res. Natl., Inst. Stand. Technol.*, vol. 104, No. 2, pp. 173-183 (Mar.-Apr. 1999).

Fornetti, Willa C., et al., "Reliability and validity of body composition measures in female athletes," Journal of Applied Physiology, vol. 87, pp. 1114-1122, (1999).

Fusch, Christoph, et al., "Neonatal Body COponsition: Dual-Energy X-Ray Absorptiometry, Magnetic Resonance Imaging, and Three-Dimensional Chemical Shift Imaging *versus* Chemical Analysis in Piglets," *Pediatric Research*, vol. 46, No. 4, pp. 465-473 (1999).

Gudivaka, R., et al., "Single- and multifrequency models for bioelectrical impedance analysis of body water compartments," *J. Appl. Physiol.*, vol. 87, No. 3, pp. 1087-1096 (1999).

Jennings, Graham, et al., "The Use of infrared Spectrophotometry for Measuring Body Water Spaces," vol. 45, No. 7, pp. 1077-1081 (1999).

Kalantar-Zadeh, Kamyar, et al., "Near infra-red interactance for nutritional assessment of dialysis patients," *Nephrol Dial Transplant*, vol. 14, pp. 169-175 (1999).

Kayser-Jones, Jeanie, et al., "Factors Contributing to Dehydration in Nursing Homes: Inadequate Staffing and Lack of Professional Supervision," *J. Am Geriatr. Soc.*, vol. 47, pp. 1187-1194 (1999).

Lange, Neale R., et al., "The Measurement of lung water," *Critical Care*, vol. 3, pp. R19-R24 (1999).

Marken Lichtenbelt, Wouter D. Van, et al., "Increased extracellular water compartment, relative to intracellular water compartment, after weight reduction," *Journal of Applied Physiology*, vol. 87, pp. 294-298 (1999).

Rennie, Michael J., "PERSPECTIVES—Teasing out the truth about collagen," *Journal of Physiology*, vol. 521, p. 1 (1999).

Sowa et al., "New-infrared spectroscopic assessment of tissue hydration following surgery", *Journal of Surgical Research*, 86:62-69 (1999).

Wagner, J.R., et al., "Analysis of Body Composition Changes of Swine During Growth and Development," *J. Anim. Sci.*, vol. 77, pp. 1442-1466 (1999).

Wang, Zimian, et al., "Hydration of fat-free body mass: new physiological modeling approach," *Am. J. Physiol.*, vol. 276, pp. E995-E1003 (1999).

Wang, Zimian, et al., "Hydration of fat-free body mass: review and critique of a classic body-composition constant," *Am J. Clin. Nutr.*, vol. 69, pp. 833-841 (1999).

Ward, L., et al., "Multiple frequency bioelectrical impedance analysis: a cross-validation study of the inductor circuit and Cole models," *Physiol. Meas.*, vol. 20, pp. 333-347 (1999).

Well, Jonathan CK, et al., "Four-component model of body composition in children: density and hydration of fat-free mass and comparison with simpler models," *Am J. Clin. Nutr.*, vol. 69, pp. 904-912 (1999).

Butte, Nancy F., et al., "Body Composition during the First 2 Years of Life; An Updated Reference," *Pediatric Research*, vol. 47, No. 5, pp. 578-585 (2000).

Feigenbaum, Matthew S., et al., "Contracted Plasma and Blood Volume in Chronic Heart Failure," *J Am Coll. Cardiol.*, vol. 35, No. 1, pp. 51-55 (Jan. 2000).

Kays, Sandra E., et al., "Predicting protein content by near infrared reflectance spectroscopy in diverse cereal food products," *J. Near Infrared Spectrosc.*, vol. 8, pp. 35-43 (2000).

Lucassen, G., et al., "Water Content and Water Profiles in Skin Measured by FTIR and Raman Spectroscopy," *Proc. SPIE*, vol. 4162, pp. 39-45 (2000).

Plank, L. D., et al., "Similarity of Changes in Body Composition in Intensive Care Patients following Severe Sepsis or Major Blunt Injury," *Annals New York Academy of Sciences*, pp. 592-602 (2000).

Ritz, P., et al., "Body Water Spaces and Cellular Hydration during Healthy Aging," *Annals New York Academy of Sciences*, pp. 474-483 (2000).

Schoeller, Dale, "Bioelectrical Impedance Analysis—What does it measure?" *Annals New York Academy of Sciences*, pp. 159-162 (2000).

Starcher, Barry C., "Lung Elastin and Matrix," *Chest*, vol. 117, No. 5, pp. 229S-234S, May 2000 Supplement.

Young, A.E.R., et al., "Behaviour of near-infrared light in the adult human head: implications of clinical near-infrared spectroscopy," *British Journal of Anaesthesia*, vol. 84, No. 1, pp. 38-42 (2000).

Zembrzuski, Cora, "Nutrition and Hydration," Best Practices in Nursing Care to Older Adults, The Hartford Institute for Geriatric Nursing, vol. 2, No. 2, Sep. 2000, 2 pages.

Attas, Michael, et al., "Visualization of cutaneous hemoglobin oxygenation and skin hydration using near-infrared spectroscopic imaging," *Skin Research and Technology*, vol. 7, pp. 238-245, (2001).

Bray, George A., et al., "Evaluation of body fat in fatter and leaner 10-y-old African American and white children: the Baton Rouge Children's Study," *Am J. Clin Nutr*, vol. 73, pp. 687-702 (2001).

Campbell, Wayne W., et al., "The Recommended Dietary Allowance for Protein May Not Be Adequate for Older People to Maintain Skeletal Muscle," *Journal of Gerontology*, vol. 56A, No. 6, pp. M373-M-380 (2001).

Divert, Victor E., "Body Thermal State Influence on Local Skin Thermosensitivity," *International Journal of Circumpolar Health*, vol. 60, pp. 305-311 (2001).

Du, Y., "Optical properties of porcine skin dermis between 900 nm and 1500 nm," *Phys. Med. Biol.*, vol. 46, pp. 167-181 (2001).

Endo, Yutaka, et al., "Water drinking causes a biphasic change in blood composition in humans," *Pflügers Arch—Eur J. Physiol*, vol. 442, pp. 362-368 (2001).

Garaulet, Marta, et al., "Site-specific differences in the fatty acid composition of abdominal adipose tissue in an obese population from a Mediterranean area: relation with dietary fatt acids, plasma lipid profile, serum insulin, and central obesity," *Am J. Clin. Nutr.*, vol. 74, pp. 585-591 (2001).

Haga, Henning A., et al., "Electroencephalographic and cardiovascular indications of nociception during isoflurane anaesthesia in pigs," *Veterinary Anaesthesia and Analgesia*, vol. 28, pp. 126-131 (2001).

Kalantar-Zadeh, Kamyar, et al., "Near infra-red interactactance for Longitudinal Assessment of Nutrition in Dialysis Patients," *Journal of Renal Nutrition*, vol. 11, No. 1, pp. 23-31 (Jan. 2001).

Kamba, Masayuki et al., "Proton magnetic resonance spectroscopy for assessment of human body composition," *Am J. Clin. Nutr.*, vol. 73, pp. 172-176 (2001).

Lever, M., et al., "Some ways of looking at compensatory kosmotropes and different water environments," *Comparative Biochemistry and Physiolog.*, vol. 130, Part A, pp. 471-486, (2001).

Mingrone, G. et al., "Unreliable use of standard muslce hydration value in obesity," *Am J. Physiol Endocrinal Metab.*, vol. 280, pp. E365-371, (2001).

Ritz, Patrick, "Chronic Cellular Dehydration in the Aged Patient," Journal of Gerontology, vol. 56A, No. 6, pp. M349-M352 (2001).

Šašic, Slobodan, et al., "Shore-Wave Near-Infrared Spectroscopy of Biological Fluids. 1. Quantitative Analysis of Fat, Protein, and Lactose in Raw Milk by Partial Least-Squares Regression and Band Assignment," *Anal. Chem.*, vol. 73, pp. 64-71 (2001).

Schnickel, A.P., et al., "Evaluation of alternative measures of pork carcass composition," *J. Anim. Sci.*, vol. 79, pp. 1093-1119, (2001).

Sowa et al., "Near infrared spectroscopic assessment of hemodynamic changes in the early post-burn period," *Burns*, 27(3):241-9 (2001).

Troy, Tamara L., et al., "Optical properties of human skin in the near infrared wavelength range of 1000 to 2200nm," *Journal of Biomedical Optics*, vol. 6, No. 2, pp. 167-176 (Apr. 2001).

Tsukahara, K., et al., "Dermal fluid translocation is an important determinant of the diurnal variation in human skin thickness," *British Journal of Dermatology*, vol. 145, pp. 590-596 (2001).

Vescovi, Jason D., et al., "Evaluation of the BOD POD for estimating percentage body fat in a heterogeneous group of adult humans," *Eur J. Appl. Physiol.*, vol. 85, pp. 326-332 (2001).

Wang, Zimian, et al., "Magnitude and variation of ratio of total body potassium to fat-free mass: a cellular level modeling study," *Am J. Physiol. Endocrinal. Metab*, vol. 281, pp. E1-E7, (2001).

Watson, Walter, "Hydration of fat-free body mass: new physiological modeling approach," *Am J. Physiol. Endocrinol. Metab.*, Letters to the Editor, vol. 278, pp. E752-E753 (2001).

Attas, E. Michael, et al., "Near-IR Spectroscopic Imaging for Skin Hydration: The Long and the Short of It," *Biopolymers*, vol. 67, No. 2, pp. 96-106 (2002).

Attas, M. et al., "Long-Wavelength Near-Infrared Spectroscopic Imaging for In-Vivo Skin Hydration Measurements," *Vibrational spectroscopy* (Feb. 28, 2002), vol. 28, No. 1, p. 37-43.

Blank, T.B., et al., "Clinical Results from a Non-Invasive Blood Glucose Monitor," *Photonics West 2002 Meeting*, San Jose, California, Jan. 19-25, 2002 (25 pages).

Chamney, Paul W., et al., "A new technique for establishing dry weight in hemodialysis patients via whole body bioimpedance," *Kidney International*, vol. 61, pp. 2250-2258 (2002).

Drobin, Dan, et al., "Kinetics of Isotonic and Hypertonic Plasma Volume Expanders," *Anesthesiology*, vol. 96, No. 6, pp. 1371-1380 (Jun. 2002).

Endo, Yutaka, et al., "Changes in Blood Pressure and Muscle Sympathetic Nerve Activity during Water Drinking in Humans," *Japanese Journal of Physiology*, vol. 52, pp. 421-427 (2002).

Haga, Henning A., et al., "Motor responses to stimulation during isoflurane anaesthesia in pigs," *Veterinary Anaesthesia and Analgesia*, vol. 29, pp. 69-75 (2002).

Klaus, Stephan, et al., "Assessment of fluid balance by measurement of skin tissue thickness during clinical anaesthesia," *Clin. Physiol. & Func. Im.*, vol. 22, pp. 197-201 (2002).

Meglinski, Igor V., et al., "Quantitative assessment of skin layers absorption and skin reflectance spectra simulation in the visible and near-infrared spectral regions," *Physiol. Meas.*, vol. 23, pp. 741-753, (2002).

Perez-de-Sà, Valéria et al., "Mild Hypothermia Has Minimal Effects on the Tolerance to Severe Progressive Normovolemic Anemia in Swine," *Anesthesiology*, Vo. 97, pp. 1189-1197 (2002).

Ponec, Maria, et al., "Charactrization of Reconstructed Skin Models," *Skin Pharmacol Appl Skin Physiol.*, vol. 15, Supplement 1, pp. 4-17, (2002).

Querleux, B., et al., "Anatomy and physiology of subcutaneous adipose tissue by in vivo magnetic resonance imaging and spectroscopy: Relationships with sex and presence of cellulite," *Skin Research and Technology*, vol. 8, pp. 118-124 (2002).

Van Bommel, Jasper, et al., "Intestinal and Cerebral Oxygenation during Severe Isovolemic Hemodilution and Subsequent Hyperoxic Ventilation in a Pig Model," *Anesthesiology*, vol. 97, No. 3, pp. 660-670 (Sep. 2002).

Wong, William W., et al., "Evaluating body fat in girls and female adolescents: advantages and disadvantages of dual-energy X-ray absorptiometry," *Am J. Clin Nutr.*, vol. 76, pp. 384-389 (2002).

Baković, Darija, et al., "Spleen volume and blood flow response to repated breath-hold apneas," *J. Appl. Physiol.*, vol. 95, pp. 1460-1466 (2003).

Bartok, Cynthia, et al., "Measurement of nutritional statusin simulated microgravity by bioelectrical impedance spectroscopy," *J. Appl. Physiol.*, vol. 95, pp. 225-232 (2003).

Bouwstra, Joke A., et al., "Water Distribution and Related Morphology in Human Stratum Corneum at Different Hydration Levels," *J. Invest Dermatol*, vol. 150, pp. 750-758 (2003).

Butte, Nancy F., et al., "Composition of gestational weight gain impacts maternal fat retention and infant birth weight," *Am J. Obstet Gynecol*, vol. 189, pp. 1423-1432 (2003).

Cloonan, Clifford C., "Don't Just Do Something, Stand There!: To Teach of not to Teach, That is the Question—Intravenous Fluid Resuscitation Training for Combat Lifesavers," *The Journal of TRAUMA, Injury, Infection, and Critical Care*, vol. 54, No. 5, pp. S20-S25 (May Supplement 2003).

Cook, Lynda S., "IV Vluid Resuscitation," *Journal of Infusion Nursing*, vol. 26, No. 5, pp. 296-303 (Sep./Oct. 2003).

Dey, D.K., et al., "Body composition estimated by bioelectric impedance in the Swedish elderly. Development of population-based prediction equation and reference values of fat-free mass and body fat for 70- and 75-y olds," *European Journal of Clinical Nutrition*, vol. 57, pp. 909-916 (2003).

Farstad, M., et al., "Fluid extravasation during cardiopulmonary bypass in piglets—effects of hypothermia and different cooling protocols," *Acta Anaesthesiol. Scand.*, vol. 47, pp. 397-406 (2003).

Grandjean et al., "Hydration: Issues for the 21$^{st}$ century", *Nutrition Reviews*, 61(8):261-271 (2003).

Heise, H.M., et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).

Kasemsumran, Sumaporn, et al., "Simultaneous determination of human serum albumin, γ- globulin, and glucose in a phosphate buffer solution by near-infrared spectroscopy with moving window partial least-squares regression," *Analyst*, vol. 128, pp. 1471-1477 (2003).

Kemming, G.I., et al., "Hyperoxic ventilation at the critical haematocrit," *Resuscitation*, vol. 56, pp. 289-297 (2003).

Kurita, T., et al., "Comparison of isoflurane and propofol-fentanyl anaesthesia in a swine model of asphyxia," *British Journal of Anaesthesia*, vol. 91, No. 6, pp. 871-877 (2003).

Laaksonen, DE, et al., "Changes in abdominal subcutaneous fat water content with rapid weight loss and long-term weight maintenance in abdominally obese men and women," *International Journal of Obesity*, vol. 27, pp. 677-683 (2003).

Mao, Jinshu, et al., "Study of Novel Chitosan-gelatin artificial skin in vitro," *J. Miomed Mater Res.*, vol. 64, Part A, pp. 301-308 (2003).

Mauran, P., et al., "Renal and hormonal responses responses to isotonic saline infusion after 3 days' dead-down tilt vs. supine and seated positions," *Acta Physiol. Scand.*, vol. 177, pp. 167-176, (2003).

McHugh, Gerard, "Letter—Passive leg elevation and head-down tilt: effects and duration of changes," *Critical Care*, vol. 7, No. 3, p. 246 (Jun. 2003).

Meglinski, I.V., et al., "Computer simulation of the skin reflectance spectra," *Computer Methods and Programs in Biomedicine*, vol. 70, pp. 179-186, (2003).

Mendelsohn, Richard, et al., "Infrared microspectroscopic imaging maps the spatial distribution of exogenous molecules in skin," *Journal of Biomedical Optics*, vol. 8, No. 2, pp. 185-190 (Apr. 2003).

Mentes, Janet C., et al., "Reducing Hydration=- Linked events in Nursing Home Residents," *Clinical Nursing Research*, vol. 12, No. 3, pp. 210-225 (Aug. 2003).

Merritt, Sean, et al., "Coregistration of diffuse optical spectroscopy and magnetic resonance imaging in a rat tumor model," *Applied Optics*, vol. 42, No. 16, pp. 2951-2959 (Jun. 2003).

Parker, Lisa, et al., "Validity of Six Field and Laboratory Methods for Measurement of Body Composition in Boys," *Obesity Research*, vol. 11, No. 7, pp. 852-858 (Jul. 2003).

Petäjä L., et al., "Dielectric constant of skin and subcutaneous fat to assess fluid changes after cardiac surgery", *Physiological Measurement*, 24:3383-390, 2003.

Richardson, Andrew D., et al., "Multivariate analyses of visible/near infrared (VIS/NIR) absorbance spectra reveal underlying spectral differences among dried, ground confier needle samples from different growth environments," *New Phytologist*, vol. 161, pp. 291-301 (2003).

Robinson, Martin P., et al., "A novel method of studying total body water content using a resonant cavity: experiments and numerical simulation," *Phys. Med. Biol.*, vol. 48, pp. 113-125, (2003).

Sergi, Giuseppe, et al., "Changes in Fluid Compartments and Body Composition in Obese Women after Weight Loss Induced by Gastric Banding," *Ann. Nutr Metab.*, vol. 47., pp. 152-157 (2003).

Wang, Zimian, et al., "Magnitude and variation of fat-free mass density: a cellular level body composition modeling study," *Am J. Physiol. Endocrinal. Metab*, vol. 284, pp. E267-E273 (2003).

Windberger, U, et al., "Whole blood viscosity, plasma viscosity and erthrocyte aggregation in nine mammalian species; reference values and comparison of data," *Exp., Physiol.*, vol. 88, No. 3, pp. 431-440 (2003).

Wolf, Martin, et al., "Absolute Frequency-Domain pulse Oximetry of the Brian: Methodology and Measurements," *Oxygen Transport to Tissue XXIV*, Chapter 7, Dunn and Swartz, Kluwer Academic/Plenum Publishers, pp. 61-73 (2003).

Ackland, G.L., et al., "Assessment of preoperative fluid depletion using bioimpedance analysis," *British Journal of Anaesthesia*, vol. 92, No. 1, pp. 134-136 (2004).

Arimoto et al., "Non-contact skin moisture measurement based on near-infrared spectroscopy", *Applied Spectroscopy*, 58(12):1439-1445 (2004).

Davidhizr, R., et al., "A review of the literature on how important water is to the world's elderly population," *International Nursing Review*, vol. 51, pp. 159-166 (2004).

Dullenkopf, A., et al., "Non-invasive monitoring of haemoglobin concentration in paediatric surgical patients using near-infrared spectroscopy," *Anaesthesia*, vol. 59, pp. 453-458 (2004).

Finlay, Jarod C., et al., "Hemoglobin oxygen saturations in phantoms and in vivo from measurements of steady-state diffuse reflectance at a single, short source-detector separation," *Medical Physics*, vol. 31, No. 7, pp. 1949-1959 (Jul. 2004).

Hendriks, F.M., et al., "Influence of hydration and experimental length scale on the mechanical response o human skin in vivo, using optical coherence tomography," *Skin Research and Technology*, vol. 10, pp. 231-241 (2004).

Hieda, I., et al., "Basic characteristics of the radio imaging method for biomedical application," *Medical Engineering & Physics*, vol. 26, pp. 431-437 (2004).

Ikizler, T. Alp, et al., "Urea space and total body water measurements by stable isotopes in patients with acute renal failure," *Kidney International*, vol. 65, pp. 725-732 (2004).

Isenring, E., et al., "Evaluation of foot-to-foot bioelectrical impedance analysis for the prediction of total body water in oncology outpatients receiving radiotherapy," *European Journal of Clinical Nutrition*, vol. 58, pp. 46-51 (2004).

Jacobi, Ute, et al., "In vivo determination of skin surface topography using an optical 3D device," *Skin Research and Technology*, vol. 10, pp. 207-214 (2004).

Kao, Bunsho, et al., "Evaluation of Cryogen Spray Cooling Exposure on In Vitro Model Human Skin," *Lasers in Surgery and Medicine*, vol. 34, pp. 146-154 (2004).

Kyle, Urusula G., et al., Bioelectrical impedance anslysis—part II: utilization in clinical practice, *Clinical Nutrition*, vol. 23, pp. 1430-1453 (2004).

Lof, Marie, et al., "Hydration of fat-free mass in healthy women with special reference to the effect of pregnancy," *Am J. Clin. Nutr.*, vol. 80, pp. 960-965 (2004).

Mirrashed, F., et al., "Pilot study of dermal and subcutaneous fat structures by MRI in individuals who differ in gender, BMI, and cellulite grading," *Skin Research and Technology*, vol. 10, pp. 161-168 (2004).

Mirrashed, Fakhereh, et al., "In vivo morphological characterization of skin by MRI micro-imaging methods," *Skin Research and Technology*, vol. 10, pp. 149-160, (2004).

Notingher, Ioan, et al., "Mid-infrared in vivo depth-profiling of topical chemicals on skin," *Skin Research and Technology*, vol. 10, pp. 113-121, (2004).

Nouveau-Richard, S., et al., "In vivo epidermal thick ness measurement: ultrasound vs. confocal imaging," *Skin Research and Technology*, vol. 10, pp. 136-140, (2004).

Nuutinen, J., et al., "Validation of a enw dielectric device to assess changes of tissue water in skin and subcutaneous fat," *Physiol. Meas.*, vol. 25, pp. 447-454, (2004).

Mirrashed, F., et al., "Pilot study of dermal and subcutaneous fat structures by MRI in individulas who differ in gender, BMI, and cellulite grading," *Skin Research and Technology*, vol. 10, pp. 161-168 (2004).

Rhodes, Andrew, et al., "Book Report—Haemodynamic monitoring in critically ill patients," *Critical Care*, vol. 8, p. 203 (2004).

Schou, A. J., et al., "Methodological aspects of high-frequency ultrasound of skin in children," *Skin Research and Technology*, vol. 10, pp. 200-206, (2004).

Stone, Darren A., et al., "Total body water measurements using resonant cavity perturbation techniques," *Phys. Med. Biol.*, vol. 49, pp. 1773-1788, (2004).

Takiwaki, Hirotsugu, et al., "Analysis of the absorbance spectra of skin lesions as a helpful tool for detection of major pathophysiological changes," *Skin Research and Technology*, vol. 10, pp. 130-135 (2004).

Van Kemenade, Patricia M., et al., "Do somotic forces play a role in the uptake of water by human skin?", *Skin Research and Technology*, vol. 10, pp. 109-112 (2004).

Wang, Zimian, et al., "Body cell mass: model development and validation at the cellular level of body composition," *Am J. Physiol. Endocrinol. Metab.*, vol. 286, pp. E123-E128 (2004).

Garcia-Olmo, J., et al., "Advantages and disadvantages of multiple linear regression and partial least squares regression equations for the prediction of fatty acids," pp. 253-258, undated.

Wang, Zimian, et al., "Cellular-Level Body Composition Model—A New Approach to Studying Fat-free Mass Hydration," *Annals New York Academy of Sciencei*, pp. 306-311, undated.

\* cited by examiner

PULSE OXIMETRY MOTION ARTIFACT REJECTION USING NEAR INFRARED ABSORPTION BY WATER

BACKGROUND OF THE INVENTION

The present invention relates to the processing of signals obtained from a medical diagnostic apparatus, such a pulse oximeter, using near infrared spectroscopy, to remove artifact or noise effects from the signal representative of a physiological parameter of interest.

A typical pulse oximeter measures two physiological parameters, percent oxygen saturation of arterial blood hemoglobin ($SpO_2$ or sat) and pulse rate. Oxygen saturation can be estimated using various techniques. In one common technique, the photocurrent generated by the photo-detector is conditioned and processed to determine the ratio of modulation ratios (ratio of ratios) of the red to infrared signals. This modulation ratio has been observed to correlate well to arterial oxygen saturation. The pulse oximeters and sensors are empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. Most pulse oximeters extract the plethysmographic signal having first determined saturation or pulse rate, both of which are susceptible to interference.

In general, pulse oximetry takes advantage of the fact that in live human tissue, hemoglobin is a strong absorber of light between the wavelengths of 500 and 1100 nm. The pulsation of arterial blood through tissue is readily measurable, using light absorption by hemoglobin in this wavelength range. A graph of the arterial pulsation waveform as a function of time is referred to as an optical plethysmograph. The amplitude of the plethysmographic waveform varies as a function of the wavelength of the light used to measure it, as determined by the absorption properties of the blood pulsing through the arteries. By combining plethysmographic measurements at two different wavelength regions, where oxy- and deoxy-hemoglobin have different absorption coefficients, the oxygen saturation of arterial blood can be estimated. Typical wavelengths employed in commercial pulse oximeters are 660 and 890 nm.

It is known that rapid motion or application of pressure to a tissue site can have the effect of changing the optical properties being measured at or near that site. The amplitude of the optical signal changes associated with such events, known as motion artifacts, can easily be larger than that due to the arterial pulse. In practice, this can lead to inaccurate estimation of the percent oxygen saturation by pulse oximetry. Various techniques for addressing and removing undesired signal effects, including motion artifacts are known. As used herein, noise refers to signal portions that are undesired or are not directly related to changes in optical properties that are related to the arterial pulse, and which may include motion artifact. The optical signal through the tissue can be degraded by both noise and motion artifact. One source of noise is ambient light which reaches the light detector. Another source of noise is electromagnetic coupling from other electronic instruments. Motion of the patient also introduces noise and affects the signal. For example, the contact between the detector and the skin, or the emitter and the skin, can be temporarily disrupted when motion causes either to move away from the skin. In addition, since blood is a fluid, it responds differently than the surrounding tissue to inertial effects, thus resulting in momentary changes in volume at the point near which the oximeter probe is attached.

Motion artifact can degrade a pulse oximetry signal relied upon by a health care provider, without the provider's awareness. This is especially true if the monitoring of the patient is remote, the motion is too small to be observed, or the health care provider is watching the instrument or other parts of the patient, and not the sensor site. There are various known techniques for addressing the effects of noise and/or motion artifacts.

For example, U.S. Pat. No. 4,714,341 discloses a method for combining three wavelengths to detect the presence of motion. The wavelengths are used two at a time to separately compute the oxygen saturation percentage. When the oxygen saturation values computed using different wavelength combinations are in poor agreement, this is assumed to be caused by motion artifact, and the value is discarded. A disadvantage of this approach is that the agreement or lack thereof between the saturation values may or may not be due to motion artifact. In addition, this approach does not identify or remove the effects of motion artifact, but instead discards values that appear suspect.

Another approach involves the filtering of pulse oximetry signals. However, filtering methods require assumptions about the properties of the artifact that do not always hold in practice. In addition, this approach does not measure the motion-induced signal.

U.S. Pat. No. 5,482,036 provides another approach, and describes a signal processing method for artifact reduction that functions when the artifact-related signal is associated with blood that is at a lower oxygen saturation than the arterial blood. Such a method relies on the generation of an artificial noise signal, which is combined with the physiological parameter to reduce the effect of the unknown noise signal. This approach for reducing the effects of artifact, without separately measuring the motion signal, is based on assumptions about the effect of motion on the plethysmographic signal. Assumptions may or may not be true, and many assumptions are invalid.

Each of the known techniques for compensating for motion artifact has its own limitations and drawbacks. It is therefore desirable that a pulse oximetry system be designed which more effectively and accurately reports blood-oxygen levels during periods of motion. While many have attempted to isolate the effects of undesired signal portions, such as motion-induced artifacts, by making potentially invalid assumptions or by rejecting suspect estimates of desired signal values, there still remains a need for a deterministic identification, determination and measurement of artifact signals, to enable an accurate measurement of the desired signal values in the presence of undesired signal portions.

BRIEF SUMMARY OF THE INVENTION

By measuring the artifact signal, the present invention allows motion artifact to be separated from the plethysmographic signal without the limiting assumptions of prior known techniques. The present invention provides methods for measuring the motion signal associated with changes in tissue optical properties and using the measurement to compensate plethysmographic measurements made at other wavelengths.

In one embodiment, the present invention provides a method of measuring a physiological parameter, including obtaining a first signal derived from electromagnetic energy transmitted through a tissue portion at a first wavelength, the first signal including a signal portion corresponding with motion-related events and a signal portion corresponding with arterial pulsation events, where at the first wavelength water is a dominant absorber of electromagnetic energy in the tissue portion; obtaining a second signal derived from electromagnetic energy transmitted through a tissue portion at a second wavelength, the second signal including a signal portion corresponding with motion-related events and a signal portion corresponding with arterial pulsation events, where at the second wavelength hemoglobin is a dominant absorber of electromagnetic energy in the tissue portion; and combining the first signal and the second signal to generate a combined plethysmograph signal, such that the combined signal has a signal portion corresponding with motion-related events that is smaller than that present in the first signal or the second signal.

At the first wavelength water is a stronger absorber of electromagnetic energy than hemoglobin in the tissue portion, and at the second wavelength hemoglobin is a stronger absorber of electromagnetic energy than water in the tissue portion.

For a fuller understanding of the nature and advantages of the embodiments of the present invention, reference should be made to the following detailed description taken in conjunction with the accompanying drawings.

DETAILED DESCRIPTION OF THE INVENTION

By measuring the artifact signal, the present invention allows motion artifact to be separated from the plethysmographic signal without the limiting assumptions of prior known techniques. The present invention provides methods for measuring the motion signal associated with changes in tissue optical properties and using the measurement to compensate plethysmographic measurements made at other wavelengths.

Figure 1:
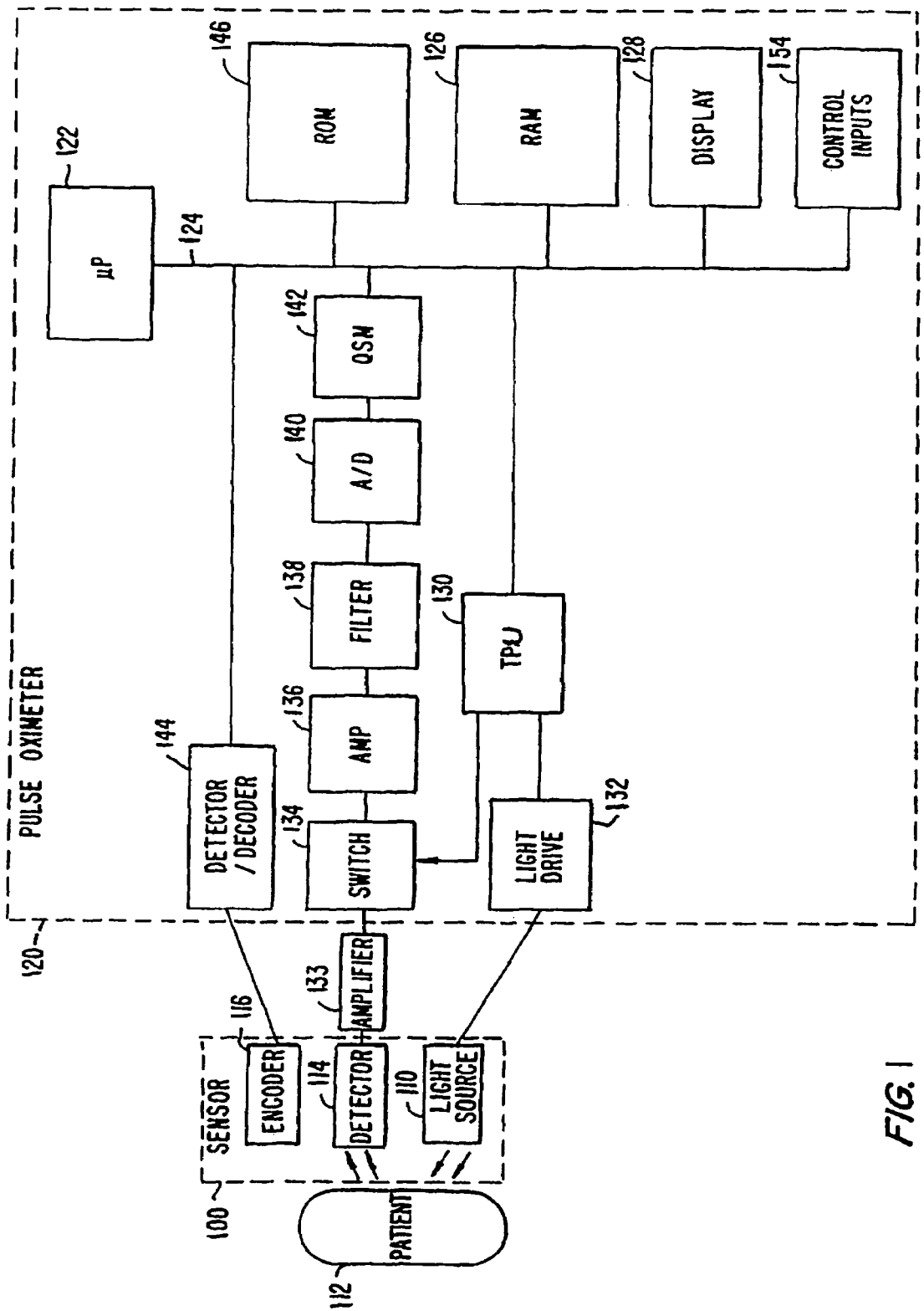
FIG. 1 is a block diagram of an exemplary oximeter.

FIG. 1 is a block diagram of an exemplary pulse oximeter that may be configured to implement the embodiments of the present invention. The embodiments of the present invention can be a data processing algorithm that is executed by the microprocessor 122, described below. Light from light source 110 passes into patient tissue 112, and is scattered and detected by photodetector 114. A sensor 100 containing the light source and photodetector may also contain an encoder 116 which provides signals indicative of the wavelength of light source 110 to allow the oximeter to select appropriate calibration coefficients for calculating oxygen saturation. Encoder 116 may, for instance, be a resistor.

Sensor 100 is connected to a pulse oximeter 120. The oximeter includes a microprocessor 122 connected to an internal bus 124. Also connected to the bus are a RAM memory 126 and a display 128. A time processing unit (TPU) 130 provides timing control signals to light drive circuitry 132 which controls when light source 110 is illuminated, and if multiple light sources are used, the multiplexed timing for the different light sources. TPU 130 also controls the gating-in of signals from photodetector 114 through an amplifier 133 and a switching circuit 134. These signals are sampled at the proper time, depending upon which of multiple light sources is illuminated, if multiple light sources are used. The received signal is passed through an amplifier 136, a low pass filter 138, and an analog-to-digital converter 140. The digital data is then stored in a queued serial module (QSM) 142, for later downloading to RAM 126 as QSM 142 fills up. In one embodiment, there may be multiple parallel paths of separate amplifiers, filters and A/D converters for multiple light wavelengths or spectra received.

Based on the value of the received signals corresponding to the light received by photodetector 114, microprocessor 122 will calculate the oxygen saturation using various algorithms. These algorithms require coefficients, which may be empirically determined, corresponding to, for example, the wavelengths of light used. These are stored in a ROM 146. In a two-wavelength system, the particular set of coefficients chosen for any pair of wavelength spectra is determined by the value indicated by encoder 116 corresponding to a particular light source in a particular sensor 100. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 154. Control inputs 154 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter. For example, the estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING," issued Dec. 29, 1998, and U.S. Pat. No. 4,911,167, entitled "METHOD AND APPARATUS FOR DETECTING OPTICAL PULSES," issued Mar. 27, 1990. Furthermore, the relationship between oxygen saturation and modulation ratio is further described in U.S. Pat. No. 5,645,059, entitled "MEDICAL SENSOR WITH MODULATED ENCODING SCHEME," issued Jul. 8, 1997.

Having described an exemplary pulse oximeter above, the methods for reducing noise, including motion artifact effects in the received signals, according to embodiments of the present invention, are described below.

Figure 2:
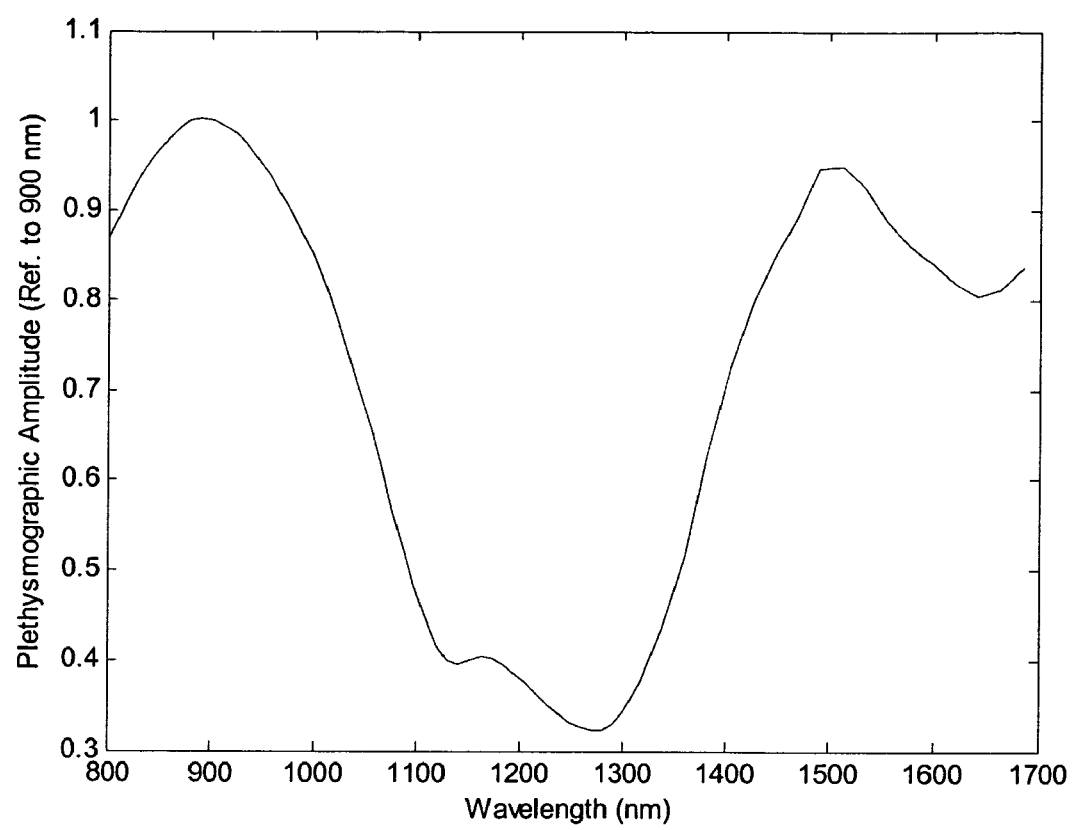
FIG. 2 is a graph of the plethysmographic amplitude measured on the human ear as a function of wavelength.
Figure 3:
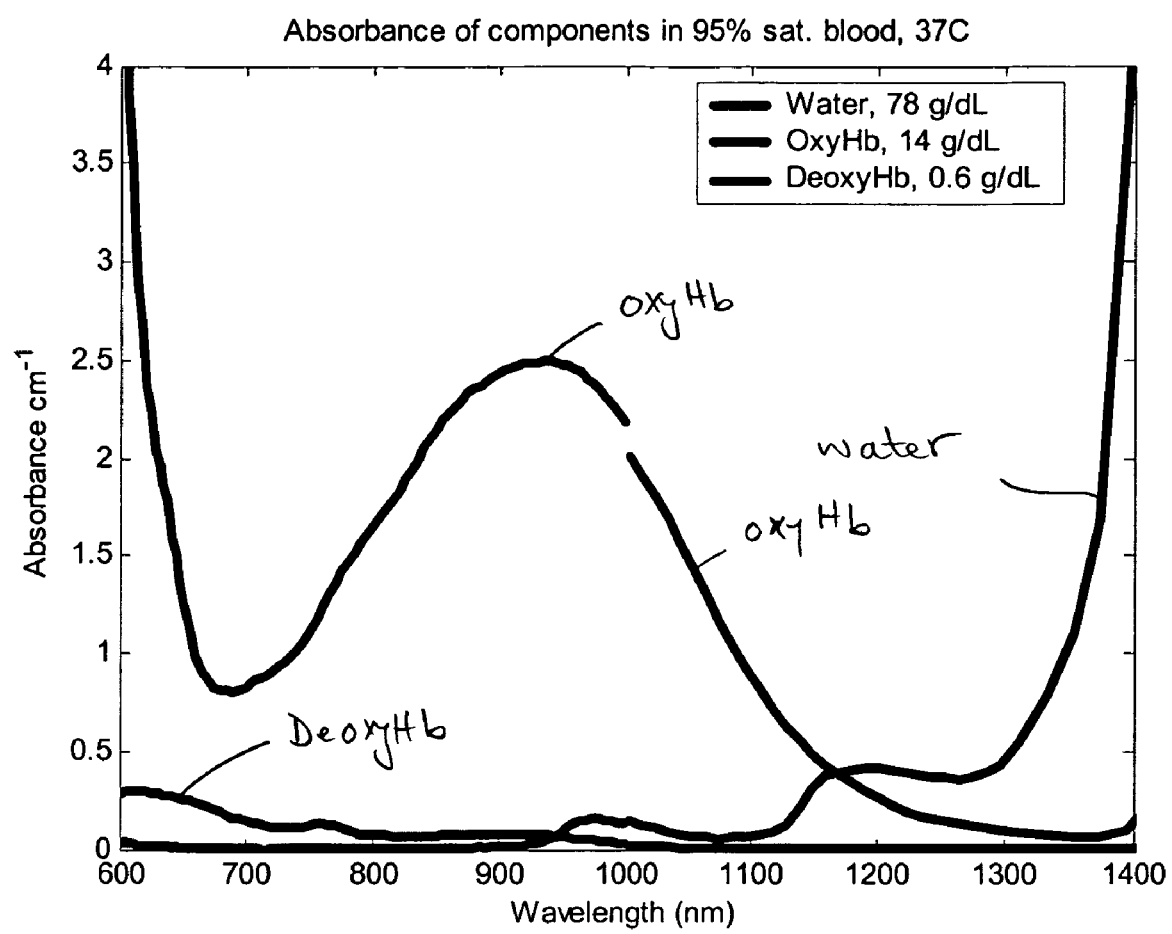
FIG. 3 is a graph of absorption spectra of the principal components in human blood.

FIG. 2 is a plot of the average plethysmographic amplitude as a function of wavelength measured through the earlobe of 36 subjects, and normalized to measurements at a wavelength of approximately 900 nm. Measurements, such as those shown in FIG. 2, reveal that the amplitude of the photoplethysmographic waveform diminishes as a function of wavelength between approximately 900 and 1300 nm, having a minimum value at approximately 1285 nm. The inventors herein have discovered that at wavelengths beyond approximately 900-920 nm, water, which is at much higher concentrations than hemoglobin, also becomes a major light absorber in tissue. FIG. 3 is a graph of some of the light absorbing components found in blood, in units of absorbance in cm$^{-1}$ vs. wavelength in nm. FIG. 3 shows that at approximately 1400 nm, the absorbance of water is approximately 60% higher than that of oxy-hemoglobin, yet the plethysmographic amplitude (FIG. 2) at 1400 nm is 35% lower than that at approximately 900 nm.

Figure 4:
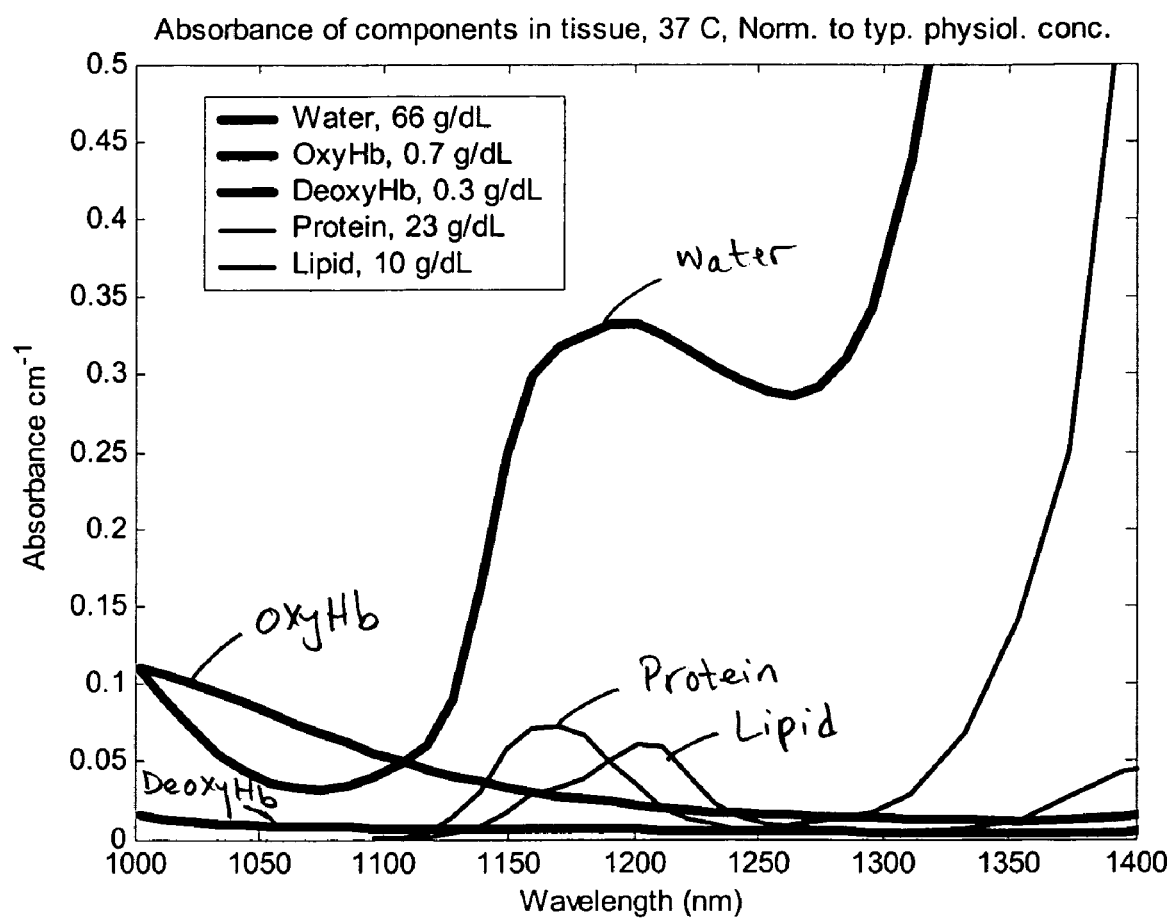
FIG. 4 is a graph of absorption spectra of the principal components in human skin, scaled to typical physiological concentration.

FIG. 4 is a graph of absorption spectra (cm$^{-1}$) of the principal components in human skin, scaled to typical physiological concentration, as a function of wavelength in nm. This figures shows that the absorbance due to water has a peak value at approximately 1180 nm, and that similar peaks are present for protein at slightly above 1150 and for lipids at approximately 1200 mm.

Figure 5:
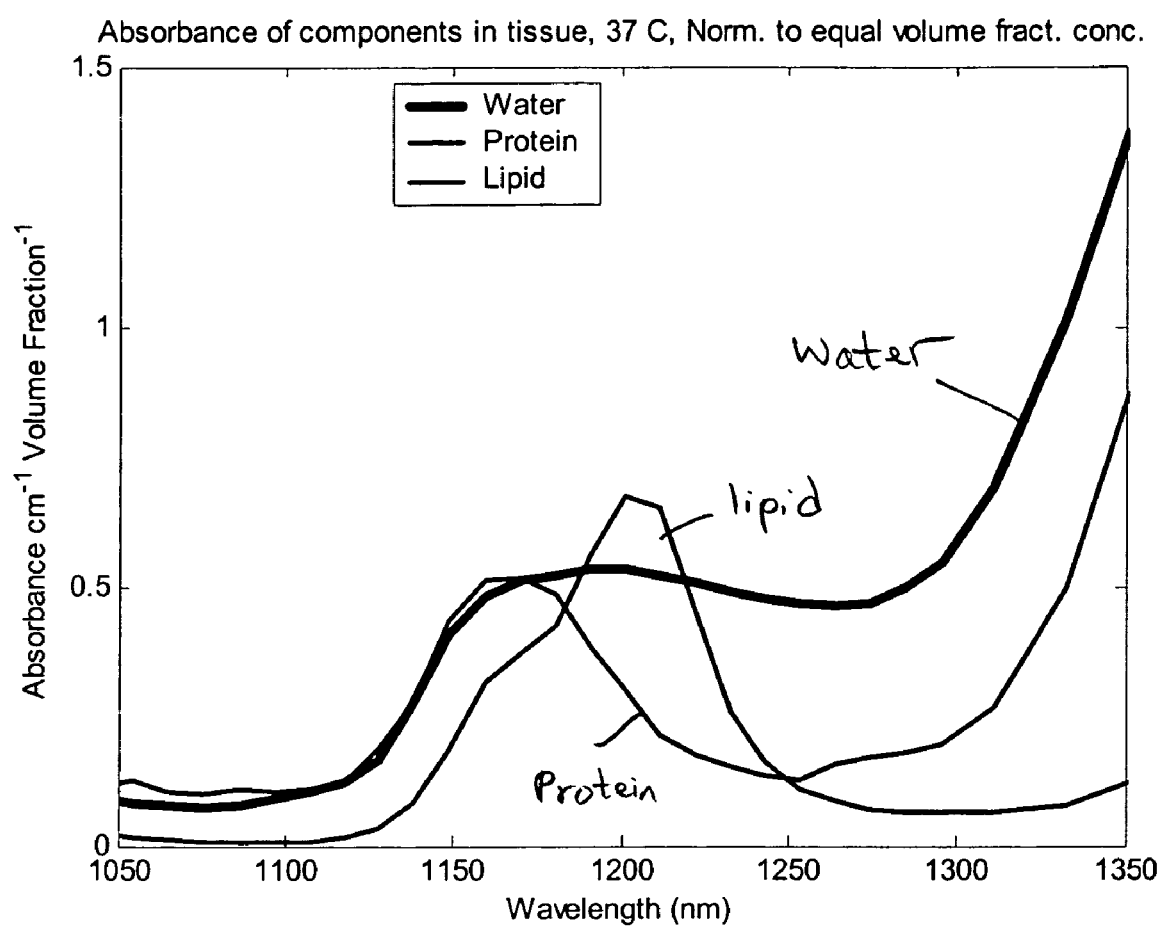
FIG. 5 is a graph of absorption spectra of the principal components in human skin, scaled to equal volume-fraction concentration.

FIG. 5 is a graph of absorption spectra of the principal components in human skin, scaled to equal volume-fraction concentration. This figure shows that at approximately 1185 nm, the volume-fraction scaled absorbance for water, lipids and proteins are approximately equal.

While not being limited to any particular theory, the present inventors note that a reason for the weaker plethysmographic effect of water (at wavelengths below approximately 900 and below approximately 1300 nm) compared to hemoglobin lies in the fact that hemoglobin is largely confined to the blood vessels, whereas water is present at high concentrations both in the blood vessels and in the surrounding tissue. As a result, the pulse-induced expansion of arterial vessels through a tissue bed results in a localized increase in hemoglobin concentration, but only a small net change in water concentration. To the extent that the water concentration in the blood is equal to the water concentration in tissue, the change in light absorption by water is expected to approach zero.

The embodiments of the present invention exploit the finding that in spectral regions where hemoglobin absorbs weakly and water absorbs strongly, the plethysmograph is more sensitive to motion-related events than arterial pulsation, compared with spectral regions where hemoglobin is a strong absorber and water is a weak absorber.

Figure 6:
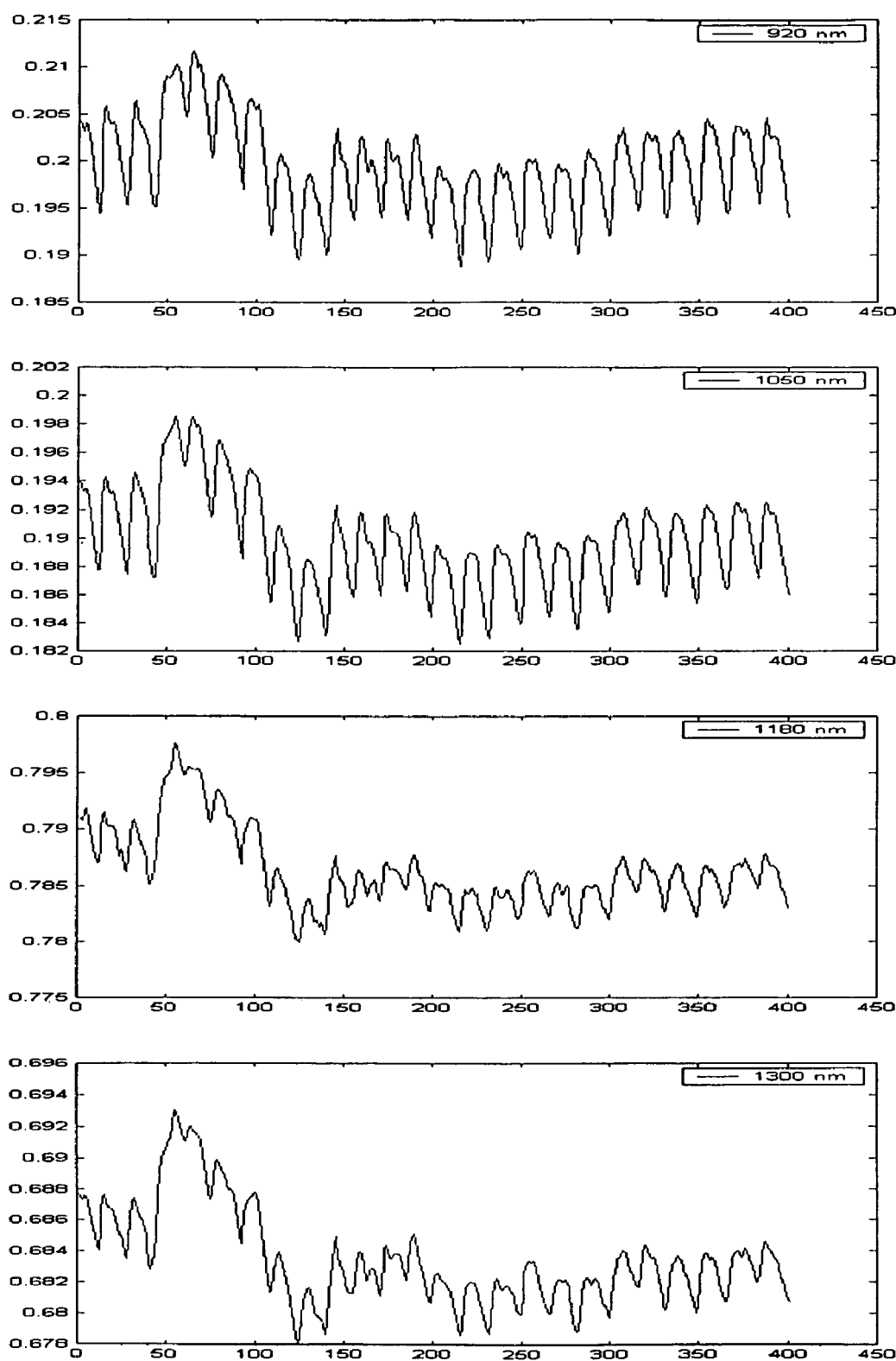
FIG. 6 is a graph of plethysmographs measured on a human ear at 4 different wavelengths of approximately 920, 1050, 1180 and 1300 nm respectively.

The weak magnitude of the plethysmograph in regions of strong water absorption is exploited to enable the separation of arterial-pulse-related signal from a motion artifact signal. By measuring the optical plethysmograph at a wavelength where water is the dominant absorber, the change in tissue optical properties associated with motion or pressure can be measured, with little interference from the underlying arterial pulsation. Plethysmographs at four near-infrared wavelengths measured through a human ear undergoing occasional motion are shown in FIG. 6, in absorbance units vs. scaled time (i.e., time per point is 43 ms). At approximately 920 nm, where hemoglobin absorption is strong and water absorption is weak, the plethysmograph contains regular arterial pulsations that are interrupted occasionally by motion-related events. As the wavelength is increased to approximately 1300 nm, where water is the predominant absorber, the arterial pulsations diminish and the measured signal becomes largely due to the motion-related events.

Figure 7:
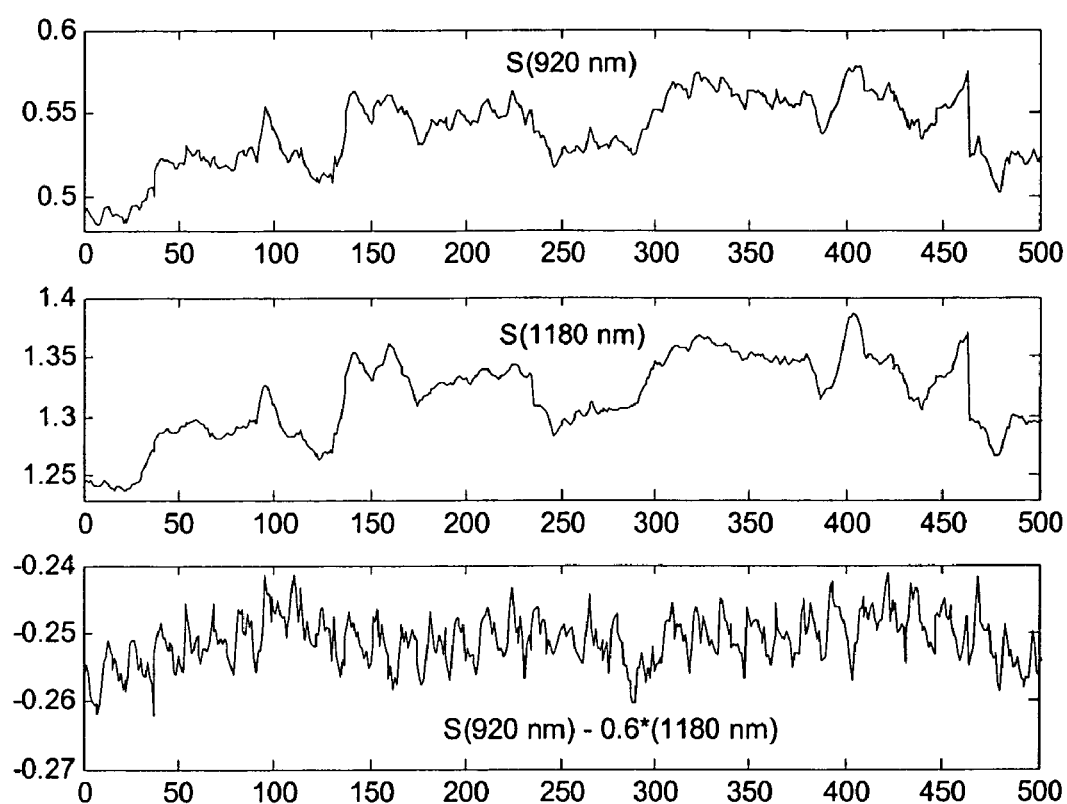
FIG. 7 is a graph of an exemplary plethysmographic artifact reduction by combining measurements at 2 near infrared wavelengths.

By combining the plethysmograph measured in a spectral region where water is the dominant absorber with a plethysmograph measured where blood is a major absorber, the motion-related signal can be selectively removed. FIG. 7 shows the plethysmograph of a human ear measured at approximately 920 nm, and the result of subtracting a portion of the plethysmograph measured at approximately 1180 nm from that measured at 920 nm. In particular, FIG. 7 shows the plethysmograph of a human ear measured at 920 nm, and the result of subtracting approximately 60% of the plethysmograph measured at approximately 1180 nm from that measured at approximately 920 nm. The 60% value is chosen since at this wavelength, the absorbance of water is approximately 60% higher than that of oxy-hemoglobin. For different wavelength combinations, other multipliers are used based on the ratios of the absorbance of water as compared to that of oxy-hemoglobin or based on empirical determination(s).

By applying the same analysis to a diverse pool of 36 patients measured in a hospital setting, an average signal to noise increase of a factor of 2 of the plethysmograph at 910 nm was observed. By allowing the multiplier for the 1180 nm plethysmograph to vary, higher signal to noise improvements are achieved.

Theoretical Model

The following derivation demonstrates a mechanism by which the effect of motion-induced changes in optical scattering on a plethysmograph measured at one wavelength can be compensated by plethysmographic measurement at a second wavelength. This derivation is provided as one example of the type of motion-induced optical changes that can be compensated, but is not the only mechanism by which the present invention may function, and thus is not meant to limit the embodiments of the present invention.

A starting point for the analysis is the diffusion theory of light transport in tissue (for example, see "Diffusion Theory of Light Transport", Willem M. Star, in Optical-Thermal Response of Laser-Irradiated Tissue, edited by Ashley J. Welch and Martin J. C. van Gemert, Plenum Press, New York, 1995, pgs. 131-206). In the case where the transport-corrected scattering coefficient, $\mu'_s$, is much larger than the absorption coefficient, $\mu_a$, the diffuse intensity of light, $I(\lambda)$, measured at wavelength, $\lambda$, by a detector positioned a distance, l, away from a light source, can be described as follows (for example, see "Measurement of Blood Hematocrit by Dual-Wavelength Near-IR Photoplethysmography", Schmitt, J. M.; Guan-Xiong, G.; Miller, J., SPIE, Vol. 1641, 1992, pgs. 150-161):

$$I(\lambda) \propto \exp(-l\sqrt{3\mu_a(\lambda)\mu'_s(\lambda)}) \qquad \text{(eqn. 1)}$$

For small changes in the absorption coefficient, such as those caused by arterial pulsation, the resulting change in intensity can be described by the derivative of intensity with respect to the absorption coefficient:

$$\frac{\frac{dI(\lambda)}{d\mu_a(\lambda)}}{I(\lambda)} = \frac{AC(\lambda)}{DC(\lambda)} = -l\sqrt{\frac{3\mu'_s(\lambda)}{4\mu_a(\lambda)}} \Delta V^{art} \mu_a^{art}(\lambda) \qquad \text{(eqn. 2)}$$

where $\Delta V^{art}$ is the fractional volume change due to arterial pulsation, $\mu_a^{art}$ is the absorption coefficient of the arterial blood under measurement, AC ($\lambda$) refers to the time varying portion of the optical signal and DC ($\lambda$) refers to the average or non-time varying portion of the optical signal.

The arterial oxygen saturation, SpO$_2$, is estimated if the AC-DC ratio described by equation 2 is measured at two wavelengths, $\lambda_1$ and $\lambda_2$, that are chosen so that oxy- and deoxy-hemoglobin are readily differentiated (e.g., $\lambda_1$~approximately 660 nm, $\lambda_2$~approximately 910 nm):

$$R = \frac{\frac{AC(\lambda_1)}{DC(\lambda_1)}}{\frac{AC(\lambda_2)}{DC(\lambda_2)}} = \Omega_{12}\frac{\mu_a^{art}(\lambda_1)}{\mu_a^{art}(\lambda_2)} \quad \text{(eqn. 3a)}$$

$$\text{where: } \Omega_{12} = \sqrt{\frac{\mu_s'(\lambda_1)\mu_a(\lambda_2)}{\mu_s'(\lambda_2)\mu_a(\lambda_1)}} \quad \text{(eqn. 3b)}$$

from which:

$$SpO_2 = \frac{\mu_a^{HHb}(\lambda_1) - R\Omega_{12}^{-1}\mu_a^{HHb}(\lambda_2)}{R\Omega_{12}^{-1}(\mu_a^{O2Hb}(\lambda_2) - \mu_a^{HHb}(\lambda_2)) + \mu_a^{HHb}(\lambda_1) - \mu_a^{O2Hb}(\lambda_1)} \quad \text{(eqn. 3c)}$$

where $\mu_a^{HHb}$ and $\mu_a^{O2Hb}$ are the respective absorption coefficients for deoxy- and oxy-hemoglobin in arterial blood, and R is the ratio of the AC to DC ratios.

The effect of small changes in the scattering coefficient, such as may be brought about by compression of tissue or motion artifact, are as set forth below by eqn. 4:

$$\frac{dI(\lambda)}{\frac{d\mu_s'(\lambda)}{I(\lambda)}} = \frac{AC(\lambda)}{DC(\lambda)} = -l\sqrt{\frac{3\mu_a(\lambda)}{4\mu_s'(\lambda)}}\Delta\mu_s'(\lambda) \quad \text{(eqn. 4)}$$

By measuring the AC-DC ratio at a third wavelength, $\lambda_3$, chosen so that the absorption due to hemoglobin is weak but the absorption due to water is strong, the effect of the motion-induced scattering change are removed from the AC-DC measurement at $\lambda_2$ by subtracting the scaled AC-DC measurement at $\lambda_3$. The resulting motion-corrected plethysmograph, P, can be expressed as:

$$P = \frac{AC(\lambda_2)}{DC(\lambda_2)} - \frac{AC(\lambda_3)}{DC(\lambda_3)}\Omega_{23}^{-1} \quad \text{(eqn. 5a)}$$

$$\text{where: } \Omega_{23} = \sqrt{\frac{\mu_s'(\lambda_2)\mu_a(\lambda_3)}{\mu_s'(\lambda_3)\mu_a(\lambda_2)}} \quad \text{(eqn. 5b)}$$

When the effects of arterial pulsation (equation 2) and motion artifact (equation 4) are additive, equation 5 is expanded as follows:

$$P = -l\sqrt{\frac{3\mu_s'(\lambda_2)}{4\mu_a(\lambda_2)}}\Delta V^{art}\mu_a^{art}(\lambda_2) - l\sqrt{\frac{3\mu_a(\lambda_2)}{4\mu_s'(\lambda_2)}}\Delta\mu_s'(\lambda_2) + \Omega_{23}^{-1}\left[l\sqrt{\frac{3\mu_s'(\lambda_3)}{4\mu_a(\lambda_3)}}\Delta\mu_a(\lambda_3) + l\sqrt{\frac{3\mu_a(\lambda_3)}{4\mu_s'(\lambda_3)}}\Delta\mu_s'(\lambda_3)\right] \quad \text{(eqn. 6)}$$

When water absorption dominates the absorption of light by tissue at $\lambda_3$, and the water concentration in the arteries and surrounding tissue is nearly equal, $\Delta\mu_a(\lambda_3)$ is approximately zero, and equation 6 simplifies to:

$$P = -l\sqrt{\frac{3\mu_s'(\lambda_2)}{4\mu_a(\lambda_2)}}\Delta V^{art}\mu_a^{art}(\lambda_2) \quad \text{(eqn. 7)}$$

Equation 7 depends only on the effect of arterial pulsation at $\lambda_2$; the effect of the motion artifact has been removed. In a similar manner the plethysmograph measured at $\lambda_3$ may be used to remove the motion effects from the plethysmograph measured at $\lambda_1$. The corrected plethysmographs measured at $\lambda_1$ and $\lambda_2$ may then be combined and used to estimate oxygen saturation, as described, for example, by equation 3.

Several wavelengths in the range between approximately 900 and 1300 nm and more specifically in the range between approximately 1150 and 1350 nm have been tested and found effective at reducing motion-artifact from plethysmographs measured at approximately 910 nm. Wavelengths at the longer wavelength side of this range have the advantage of weaker absorbance of hemoglobin compared to that of water (for example, see FIGS. 3 and 4). However, wavelengths at the shorter end of this range have the advantage of reduced variation with changing tissue composition. As can be seen in FIG. 5, where the major components of tissue have been normalized to equal volume fraction, water, lipid, and non-hemoglobin protein all have approximately equal absorbance at approximately 1185 nm. Therefore the absorbance of tissue at approximately 1185 nm will vary little with changes in the relative concentration of these principal components.

It is known that the detection of light beyond approximately 1100 nm cannot readily be accomplished with the silicon (Si) detectors that are commonly employed in commercial oximeters. For example, the detector used to collect the data displayed in FIGS. 2-7 employed Indium Gallium Arsenide (InGaAs) as the photosensitive material. The most common type of InGaAs detectors are sensitive to light between approximately 800 and 1700 nm. Therefore, in a pulse oximeter designed in accordance with the embodiments of the present invention, with the conventional wavelengths of 660 and 890 nm, in addition to a new light source that emits at wavelengths that are absorbed strongly by water (such as approximately 1180 nm or approximately between 900-1400 nm), an additional detector(s) is used. One such scheme employs two detectors, one Si and one InGaAs, placed side-by-side. An alternative arrangement uses a collinear ("sandwich") detector containing separate Si and InGaAs layers, such as those commercially available, for example, from the Hamamatsu corporation. Alternately, a germanium detector (Ge) is used as a substitute for the InGaAs detector.

In addition, an alternative to the above-described augmentation to conventional pulse oximetry, is an all-NIR pulse oximeter. An example of an all NIR oximeter is an oximeter employing light sources emitting at approximately 940, 1040, and 1180 nm used in conjunction with a single InGaAs detector. In addition to the advantage of requiring only one detector, the all-NIR implementation has advantages associated with the optical properties of tissue. The accuracy of measurements made using pulse oximetry depends, in part, on the extent to which the paths traveled by the different colors of light are the same. The mean path length and penetration depth of light at a particular wavelength traveling through tissue is strongly affected by the absorption and scattering coefficients of tissue at that wavelength. In conventional pulse oximetry, in order to achieve the same mean path length and penetration depth at two wavelengths, the scattering and absorption coefficients at the two wavelengths need to be matched. The scattering of light by tissue decreases rapidly as a function of wavelength, with the result that the scattering properties of tissue at approximately 940, 1040, and 1180 nm will be more closely matched than the scattering properties of tissue at a combination of both visible and NIR wavelengths such as approximately 660, 890, and 1180 nm, for reasons discussed below. The absorption properties of oxy- and deoxy-hemoglobin are such that at high oxygen saturation values the net (i.e., combined effects of oxy and deoxy) absorption coefficient due to hemoglobin will be matched reasonably well at 660 nm and 940 nm. However, as oxygen saturation values decrease, the high absorption coefficient of deoxy-hemoglobin at approximately 660 nm will result in an increasingly strong mismatch between the net absorption coefficient of hemoglobin at approximately 660 and approximately 940 nm. The net absorption coefficients of hemoglobin at approximately 940 and approximately 1040 nm, will be more closely matched than at approximately 660 and approximately 940 nm, over the full range of measurable oxygen saturation values.

The choice of the wavelength used to measure the motion-artifact signal depends partially on the need for matching the optical path length to that of the signals to be corrected. Beyond approximately 950 nm, the absorption coefficient of water, protein, and non-hemoglobin protein, in addition to that of hemoglobin needs to be considered in order to achieve close matching of path lengths. Although about 1185 nm is a currently preferred wavelength for measuring the motion-artifact signal, other alternative wavelength values are also effective, for example, wavelengths between approximately 1050 and 1400 nm and between approximately 1500 and 1850 nm.

The embodiments of the present invention may be practiced by placing the optical components directly at the tissue interface, or alternatively, by transporting the light to and from the tissue with fiber optics. The former implementation has the advantage of more efficient delivery and collection of the light, whereas the latter implementation has the advantages of being less costly. The less costly solution is enabled by the fact that when employing fiber optic delivery, the light sources and detectors can reside in the monitor as opposed to the sensor, and considering that such components may be more expensive that the fiber, this will result in a less expensive device.

The embodiments of the present invention have several advantages over known methods of addressing the results of motion artifacts, as discussed below. The embodiments of the present invention provide methods and devices for measuring the motion signal associated with changes in tissue optical properties and using the measurement to compensate plethysmographic measurements made at other wavelengths. By measuring the artifact signal, the embodiments of the present invention allow motion artifact to be separated from the plethysmographic signal without the limiting assumptions of the prior known techniques. Embodiments of the present invention have the advantage that in addition to identifying the motion, they provide a method of removing the motion artifact and continuing to measure the oxygen saturation during the motion.

As will be understood by those skilled in the art, other equivalent or alternative methods for the measurement of motion artifact signal associated with changes in tissue optical properties, and using the measurement to compensate plethysmographic measurements made at other wavelengths, according to the embodiments of the present invention can be envisioned without departing from the essential characteristics thereof. For example, a combination of visible and NIR or an all NIR wavelength combination may be used to make the measurements. Moreover, individuals skilled in the art of near-infrared spectroscopy would recognize that additional terms can be added to the algorithms used herein to incorporate reflectance measurements made at additional wavelengths and thus improve accuracy further. Also, light sources or light emission optics other then LED's including and not limited to incandescent light and narrow-band light sources appropriately tuned to the desired wavelengths and associated light detection optics may be placed near the tissue location or may be positioned within a remote unit; and which deliver light to and receive light from the tissue location via optical fibers. Additionally, sensor arrangements functioning in a back-scattering or a reflection mode to make optical measurements of reflectances, as well as other embodiments, such as those working in a forward-scattering or a transmission mode may be used to make these measurements. These equivalents and alternatives along with obvious changes and modifications are intended to be included within the scope of the present invention. Accordingly, the foregoing disclosure is intended to be illustrative, but not limiting, of the scope of the invention which is set forth in the following claims.

What is claimed is:

1. A method of measuring a physiological parameter, comprising:
   obtaining a first signal derived from electromagnetic energy transmitted through a tissue portion at a first wavelength, said first signal including a signal portion corresponding with motion-related events and a signal portion corresponding with arterial pulsation events, wherein at said first wavelength water is a dominant absorber of electromagnetic energy in the tissue portion;
   obtaining a second signal derived from electromagnetic energy transmitted through a tissue portion at a second wavelength, said second signal including a signal portion corresponding with motion-related events and a signal portion corresponding with arterial pulsation events, wherein at said second wavelength hemoglobin is a dominant absorber of electromagnetic energy in the tissue portion; and
   combining said first signal and said second signal to generate a combined signal comprising a plethysmograph, said combined signal having a signal portion corresponding with motion-related events that is smaller than that present in said first signal or said second signal.

2. The method of claim 1 wherein at said first wavelength water is a stronger absorber of electromagnetic energy than hemoglobin in the tissue portion.

3. The method of claim 1 wherein at said second wavelength hemoglobin is a stronger absorber of electromagnetic energy than water in the tissue portion.

4. The method of claim 1 wherein the first wavelength is in the range between approximately 1500 and 1850 nm.

5. The method of claim 1 wherein said first wavelength is in the range between approximately 1100 and 1400 nm.

6. The method of claim 1 wherein said first wavelength is in the range between approximately 1150 and 1250 nm.

7. The method of claim 1 wherein said first wavelength is approximately 1185 nm.

8. The method of claim 1 wherein said second wavelength is in the range between approximately 600 and 950 nm.

9. The method of claim 1 wherein said combing comprises applying a multiplier to said first signal to obtain a scaled first signal and subtracting the scaled first signal from said second signal.

10. The method of claim 9 wherein said multiplier is a function of the ratio of the absorption of electromagnetic energy in the tissue portion by hemoglobin at said first wavelength to that at said second wavelength.

11. The method of claim 1 wherein said physiological parameter is a pulse rate.

12. The method of claim 1 further comprising:
obtaining a third signal derived from electromagnetic energy transmitted through a tissue portion at a third wavelength, said third signal including a signal portion corresponding with motion-related events and a signal portion corresponding with arterial pulsation events, wherein at said third wavelength hemoglobin is a dominant absorber of electromagnetic energy in the tissue portion; and
combining said first signal and said third signal to generate a second combined signal comprising a plethysmograph, said second combined signal having a signal portion corresponding with motion-related events that is smaller than that present in said first signal or said third signal.

13. The method of claim 12 further comprising: combining said combined signal with said second combined signal to form a combination; and estimating an oxygen saturation value using said combination.

14. An apparatus for measuring a physiological parameter, comprising:
means for obtaining a first signal derived from electromagnetic energy transmitted through a tissue portion at a first wavelength, said first signal including a signal portion corresponding with motion-related events and a signal portion corresponding with arterial pulsation events, wherein at said first wavelength water is a dominant absorber of electromagnetic energy in the tissue portion;
means for obtaining a second signal derived from electromagnetic energy transmitted through a tissue portion at a second wavelength, said second signal including a signal portion corresponding with motion-related events and a signal portion corresponding with arterial pulsation events, wherein at said second wavelength hemoglobin is a dominant absorber of electromagnetic energy in the tissue portion; and
means for combining said first signal and said second signal to generate a combined signal comprising a plethysmograph, said combined signal having a signal portion corresponding with motion-related events that is smaller than that present in said first signal or said second signal.

15. The apparatus of claim 14 wherein said means for obtaining a first signal comprise: light emission optics configured to direct electromagnetic energy at said tissue location; and light detection optics configured to receive radiation from said tissue location.

16. The apparatus of claim 15 wherein said light emission optics are configured to deliver electromagnetic energy at a wavelength in the range between approximately 1500 and 1850 nm.

17. The apparatus of claim 15 wherein said light emission optics are configured to deliver electromagnetic energy at a wavelength in the range between approximately 1100 and 1400 nm.

18. The apparatus of claim 15 wherein said light emission optics are configured to deliver electromagnetic energy at a wavelength in the range between approximately 1150 and 1250 nm.

19. The apparatus of claim 15 wherein said light emission optics are configured to deliver electromagnetic energy at approximately 1185 nm.

20. The apparatus of claim 14 wherein said means for combining comprises means for applying a multiplier to said first signal to obtain a scaled first signal and subtracting the scaled first signal from said second signal.

21. The apparatus of claim 14 wherein said means for combining comprises a processing device configured to combine said first signal and said second signal to generate a combined signal comprising a plethysmograph, said combined signal having a signal poltion corresponding with motion-related events that is smaller than that present in said first signal or said second signal.

22. The apparatus of claim 14 further comprising:
means for obtaining a third signal derived from electromagnetic energy transmitted through a tissue portion at a third wavelength, said third signal including a signal portion corresponding with motion-related events and a signal portion corresponding with arterial pulsation events, wherein at said third wavelength hemoglobin is a dominant absorber of electromagnetic energy in the tissue portion; and
means for combining said first signal and said third signal to generate a second combined signal comprising a plethysmograph, said second combined signal having a signal portion corresponding with motion-related events that is smaller than that present in said first signal or said third signal.

23. The apparatus of claim 22 further comprising: means for combining said combined signal with said second combined signal to form a combination; and means for estimating an oxygen saturation value using said combination.

24. The apparatus of claim 14 wherein said physiological parameter is a pulse rate.

25. A method of measuring a physiological parameter, comprising:
obtaining a first absorbance signal at a first wavelength, wherein at the first wavelength water is a dominant absorber of electromagnetic energy;
obtaining a second signal at a second wavelength, wherein at the second wavelength hemoglobin is a dominant absorber of electromagnetic energy;
obtaining a third signal at a third wavelength, wherein at the third wavelength hemoglobin is a dominant absorber of electromagnetic energy;
combining the first signal and the second signal to generate a first combined signal having a signal portion corresponding with motion-related events that is smaller than that present in the second signal;
combining the first signal and the third signal to generate a second combined signal having a signal portion corresponding with motion-related events that is smaller than that present in the third signal; and
using the first combined signal with the second combined signal to estimate an oxygen saturation value.

* * * * *